United States Patent [19]
Suhonen et al.

[11] Patent Number: 5,842,489
[45] Date of Patent: Dec. 1, 1998

[54] TEXTURIZED DENTAL FLOSS AND METHOD OF MAKING

[75] Inventors: Christopher Suhonen, Guaruja; Esdras Del Soli das Dores, Sao Paulo, both of Brazil

[73] Assignee: Colgate-Palmolive Company, New York, N.Y.

[21] Appl. No.: 648,332

[22] Filed: May 15, 1996

[51] Int. Cl.⁶ .................................................. A61C 15/00
[52] U.S. Cl. .......................................... 132/321; 132/329
[58] Field of Search ..................... 132/321, 329

[56] References Cited

U.S. PATENT DOCUMENTS

| | | | |
|---|---|---|---|
| 2,667,443 | 1/1954 | Ashton | 132/321 |
| 3,837,351 | 9/1974 | Thornton . | |
| 3,896,824 | 7/1975 | Thornton . | |
| 4,008,727 | 2/1977 | Thornton . | |
| 4,029,113 | 6/1977 | Guyton | 132/321 |
| 4,034,771 | 7/1977 | Guyton | 132/321 |
| 4,142,538 | 3/1979 | Thornton . | |
| 4,277,297 | 7/1981 | Thornton . | |
| 5,284,169 | 2/1994 | Gilligan et al. | 132/321 |
| 5,311,890 | 5/1994 | Thornton . | |
| 5,353,820 | 10/1994 | Suhonen et al. | 132/321 |
| 5,357,990 | 10/1994 | Suhonen et al. | 132/321 |

FOREIGN PATENT DOCUMENTS

| | | |
|---|---|---|
| 495661 | 11/1977 | Australia . |
| WO 93/22985 | 11/1993 | WIPO . |
| WO 95/32684 | 12/1995 | WIPO . |

*Primary Examiner*—Nicholas D. Lucchesi
*Attorney, Agent, or Firm*—Michael McGreal

[57] ABSTRACT

The floss is of a yarn type that has a first thickness when under no tension and a considerably diminished thickness when under tension. The thickness of the floss can be decreased to as low as 10 percent of the thickness of the relaxed floss. This allows for easier insertion into interdental spaces. This floss is produced by coating a yarn and curing the coating on the yarn while the yarn is under minimal tension. This preserves the elasticity of the yarn and the property of the yarn having a range of thickness from a point of relaxation to a point of being under tension.

23 Claims, 1 Drawing Sheet

FIG. 1

TEXTURIZED DENTAL FLOSS AND METHOD OF MAKING

FIELD OF THE INVENTION

This invention relates to a texturized dental floss, a method for making this texturized dental floss, and an apparatus that can be used to make texturized dental flosses. More particularly this invention relates to a texturized dental floss that can stretch so as to significantly vary the diameter of the dental floss and a method and apparatus for making this dental floss.

BACKGROUND OF THE INVENTION

Texturized dental flosses are used by persons who have large inter dental spaces and who have bridges and various dental prosthesis. The texturized flosses have a greater diameter and are more effective in removing food debris and other material from large inter dental spaces, from under bridges and from around various dental prosthesis. The larger diameter and the fibrous nature of the flosses provides a good cleaning action. These texturized flosses are used in many instances in conjunction with a conventional filament floss or a tape floss. The filament floss or tape floss is used to remove food debris and other material from between the tighter inter dental spaces. The use of both flosses provides for a good cleaning of all inter dental spaces, bridgework and other prosthesis prior to tooth brushing. A tooth brushing with an anti-plaque, anti-tartar, antibacterial or other dentifrice completes an effective regimen of oral care.

The state-of-the-art of texturized flosses is exemplified by the texturized flosses and the methods of making these flosses described in U.S. Pat. No. 4,008,727, U.S. Pat. No. 4,277,297 and U.S. Pat. No. 3,896,824. In U.S. Pat. No. 4,008,727 there is disclosed a texturized floss that has intermittent texturized portions and string portions. A similar texturized floss is described in U.S. Pat. No. 3,896,827. This texturized floss likewise has texturized portions and string portions. Each of these patents discloses a coating process where by the selective use of tension texturized and non-texturized portions are formed. This method for making texturized flosses with texturized portions and non-texturized portions is further described in U.S. Pat. No. 4,277,297.

These prior art texturized flosses are available in various thicknesses. However, due to the coatings on the texturized material, and the intermittent threader and texturized portions, the flosses overall are quite rigid. These texturized flosses can be in a continuous strand or in separate lengths and usually are in separate lengths. The threader portion is a stiff narrow diameter portion. The texturized floss portion will have a larger diameter portion which is a brushing portion. The thickness of the texturized portion is set in a narrow range for each floss. However, it is desired to have a texturized floss where there are large thickness changes with tension. The floss then can be used for a wide range of interdental spaces. The floss can be put under tension to aid in inserting it into larger interdental spaces or under bridges, and the tension relaxed to increase the thickness of the floss so that it fully fills the interdental space or under a bridge to better clean these areas. This is one subject of the present invention. This new floss solves the problems of the prior art texturized flosses that have essentially much less stretch and a restricted range of use. The prior art texturized flosses have a narrow range of thickness from when under tension to a relaxed condition.

BRIEF SUMMARY OF THE INVENTION

The texturized flosses of this invention solve the problem of insertion between inter dental spaces and under bridgework for effective cleaning. Further, there is no need for a floss with intermittent texturized portions and threaded portions. The full floss length is texturized. The problem is solved by using coated texturized fibers where the yarn retains substantially all its stretch properties. The texturized fibers are coated to prevent shredding and fraying during use, but in a way to retain the resiliency of the texturized fibers. This is accomplished by the coating of the fibers while the fibers are under a minimal tension. The coating apparatus puts a minimal tension on the yarn through the coating and setting operations. The fibers retain the property of being stretchable to a lesser thickness and then a full or partial relaxation to a greater thickness. In this way, a single floss product can perform the cleaning of varied inter dental and bridgework spaces. There is no need to have texturized flosses of various thicknesses. The present texturized floss can under tension be reduced to a diameter of less than about 10 percent of the diameter of the texturized floss in a relaxed condition.

The texturized flosses also can be coated with various flavorants, colorants and medicants. Due to the large surface area of the texturized flosses they can carry a larger quantity of a flavorant or medicant than conventional fiber or tape flosses. The useful medicants include fluoride, desensitizing agents, anti-plaque agents, anti-tartar agents, anti-bacterials, antiseptics, coagulants and other medicants. The flavorants include peppermint, spearmint, cinnamon and fruit flavors. The texturized floss can deliver such medicants to the teeth and to the subgingival interstitial gum regions. In delivering the medicants, the coating will be at least partially water soluble. Saliva will dissolve the coating and deliver the medicant to the teeth and/or gums. This is a very useful way to deliver medicants to the difficult to reach interstitial spaces and subgingival areas.

BRIEF DESCRIPTION OF PRE-DRAWING

FIG. 1 is a schematic diagram of the method for making the present texturized dental floss.

DETAILED DESCRIPTION OF THE INVENTION

Figure 1:
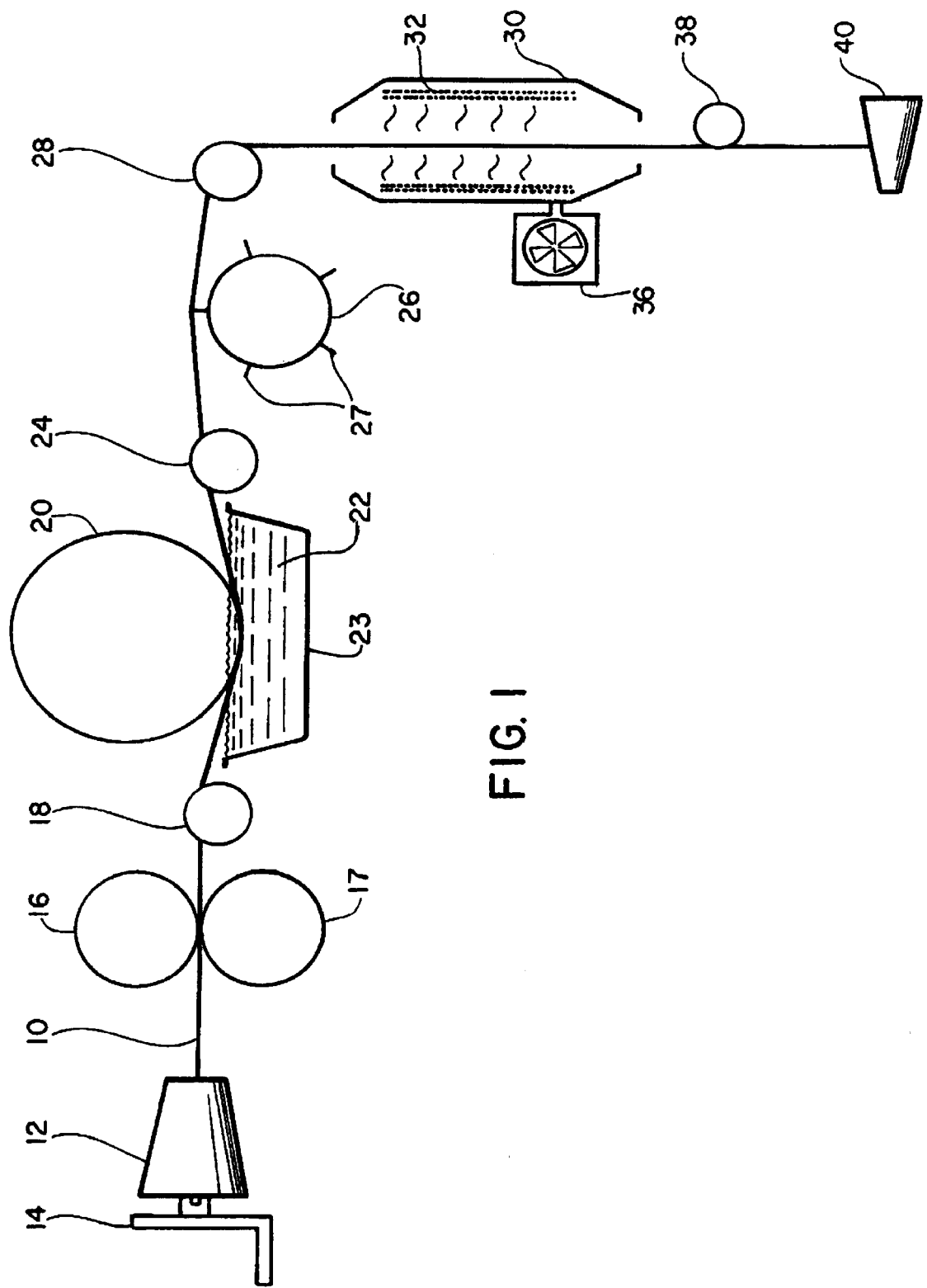

The yarn that is to be used as the floss is a particular yarn. It consists of a plurality of bundles of filaments. These are sometimes referred to as cables. In each filament bundle there can be perhaps 20 or more filaments. The filaments have been texturized by forced air, mechanical and/or heat treatments to form coils, curves, twists, crimps and/or loops. These yarns have the property of being stretchable so that the cross-sectional diameter of the yarn will be reduced when the yarn is under tension. This in combination with an irregular honeycomb surface on the yarn results in the yarn being an effective dental floss. The yarn can be tensioned to reduce its diameter to facilitate placing the yarn between a persons teeth, and then relaxed to increase the diameter for use as a floss. This cleans food debris and other materials from between close interstitial spaces.

The yarn will be comprised of about 4 to 10 filament bundles, and preferably about 6. The yarn at rest will have a cross-sectional diameter of about 10 mm to 40 mm, and preferably about 15 mm to 30 mm. In general, the yarn will approximate a circular cross-section. Upon stretching, the cross-sectional diameter of the yarn can be reduced to about as low as 10 percent of its non-tensioned diameter. In length it can be increased up to about 150 percent of its original non-tensioned length when put under tension. These are useful properties for the yarns when used as a dental floss.

The floss can be inserted into inter dental spaces when tensioned and used to remove food debris when relaxed.

The yarns cannot be used directly as a floss. There is a tendency for the yarns to shed parts of filaments. If used directly as a floss filament, parts of the yarn will be left between teeth. This is not considered to be acceptable to a person who is flossing. Consequently, the yarn is coated with a coating to lock/bond/network the filaments into a yarn. The coating preferably is a substantially water soluble polymer that will wet the filaments of the yarn and which can be set by solvent evaporation or polymerization. Non-water soluble polymers also can be used. Another type of useful polymers are ultra-violet polymerizable polymers. These set quickly upon being exposed to ultra-violet radiation. Polymers set by solvent evaporation are set by the evaporation of the solvent through heating. In any regards, the end result is a dental floss with the filaments locked into the yarn structure. However, the yarn retains its original characteristics as set out above. It is stretchable. The coated yarn under tension can acquire about as low as 10 percent of the cross-sectional diameter of the yarn at rest. And the coated yarn can stretch to more than 150 percent of its length as compared to the yarn under no tension.

The useful polymers include polyurethanes, polyesters, polyamides such as nylons, polyvinyl alcohol polymers, polyvinyl acetate polymers, and copolymers. Various polyurethanes can be ultra-violet cured to set the polymer. Useful solvent based polymers solubilized ethylene vinyl acetate copolymers and nylon dissolved in a water, ethanol, or ethanol/water mixture. When the solvent is evaporated the polymer sets to keep the filaments locked to the yarn.

An important aspect of the particular floss is setting of the coating on the yarn while the yarn is under essentially no tension. This is accomplished by the yarn essentially being only under the tension of its own weight during the setting of the polymer coating. This is a minimum tension which results in a minimum elongation during coating. The result is that during use the coated yarn can be subject to significant elongation under tension with a decrease in cross-sectional diameter to about less than 10 percent of the original diameter of the yarn. The coated yarn can be elongated under tension to more than about 150 percent of the length at rest.

FIG. 1 is a schematic diagram of the equipment suitable for coating a yarn and setting the yarn while the yarn is under a minimum of tension throughout the coating process. The yarn 10 is unwound from spool 12 which is mounted on reel 14. The yarn is removed from the spool by contact rollers 16 and 17. From this point, it is the objective to maintain the tension on the yarn at a minimum, preferably at less than about 5 grams. The yarn then passes over guide roller 18 and into coating bath 22, which is contained in trough 23. Roller 20 rotates counterclockwise and immerses the yarn in the coating. The yarn leaves trough 23 and passes over roller guide 24 and then over paddle roller 26. Paddle roller 26 has multiple paddles 27 which move the yarn in the coating process but only have a minimal contact with one side of the yarn. This paddle roller passes the yarn over guide roller 28. The yarn then passes downward under its own weight through setting chamber 30. In this embodiment, the setting chamber is a heating chamber with cylindrical heater 32 evaporating a solvent from the coating on the yarn. The blower 36 removes the solvent from the heating chamber. The yarn with a set coating leaves the heating chamber, passes over guide roller 38 and is taken up on spool 40. The yarn is wound onto spool 40 at a low tension.

If an ultra-violet radiation set polymer is used, most of the heaters in the setting chamber are replaced with ultra-violet radiation sources. In this instance, a fan 36 is used to remove any solvents emitted from the coated yarn. Many ultra-violet cured polymers contain small amounts of solvents.

The speed of travel of the yarn is about 10–70 meters per minute and preferably about 25–35 meters per minute. The take-up spool revolves at a speed of about 3 to 15 percent less than the speed of travel of the yarn, and preferably 5 to 10 percent less. When the coating solution is heat set the heater temperature is about 70 to 200 degrees centigrade, and preferably 120 to 150 degrees centigrade.

In place of being wound onto the spool the yarn can be coated with flavorants, colorants or medicants. Flavorants are usually applied in a spray dried form. Colorants are food grade dyes. Flavorants include peppermint, spearmint, cinnamon and fruit flavors. The medicants that can be applied include fluorides, bicarbonates such as sodium bicarbonate, anti-plaque agents, desensitizing agents, anti-tartar agents, antibiotics, astringents, cooling agents and coagulants. These medicants include sodium fluoride, stannous fluoride, cetylpyrdinium chloride, benzethoneum chloride, chlorhexidine, hexachlorophene, soluble pyrophosphate salts, triclosan, allantoin, zinc sulphate, menthol, tetracycline, aminocaproic acid, adrenaline and calcium alginate. Since the coated yarn has a high surface area, multi-filamentous structure it can carry comparatively high amounts of flavorants, colorants and medicants. The flavorants, colorants and medicants can be applied using any of the prior art techniques for putting such coatings onto flosses. This is accomplished very effectively through the use of water soluble polymeric coatings. These can be coatings based on polyvinyl alcohol or on polyvinyl acetate. These are water soluble polymers into which the flavorant, colorant or medicament can be dissolved or dispersed. The flavorant, colorant or medicament is coated onto the floss and the water removed to set the polymer. Other polymers also can be used.

The coatings are conveniently applied after the curing of the polymeric coating. The yarn will pass through an additional coating and heating step prior to being wound onto a spool. As noted, water based coatings are very useful. However, when the additive is compatible with the polymer coating solution in trough 23, the additive can be coated onto the yarn with the polymer coating. This will save performing an additional coating step and a heating step. This is useful with fluoride and pyrophosphate anti-tartar additives.

The present invention will be disclosed in more detail with reference to the following examples.

EXAMPLES

Example 1

A texturized nylon 6.6 yarn was coated using the apparatus of FIG. 1. The yarn consists of six plys of a 100 denier (110 decitex) texturized nylon. It has 34 filaments per ply. The final denier is 600 and decitex 660.

The polymer coating is a solution of a water and alcohol soluble polyamide. This coating solution is used at room temperature.

The texturized yarn is fed through the apparatus at 30 meters per minute. The yarn 10 is removed from spool 12 and fed to the trough 22 holding the coating solution by rollers 16 and 17. Roller 20 assures that the yarn contracts the coating solution. The coated yarn then passes over guide roller 24 and is moved along by paddle roller 26. It then passes over guide roller 28 and then downwardly through heater chamber 30 where water is removed and the coating is set. The temperature in heater chamber 30 is about 135° C.

The take-up spindle 40 is operated at 28 meters per minute. The coated yarn is now in a form useful as a floss. It is wound on smaller spools and packaged for sale.

Example 2

Some of the coated floss from Example 1 is further coated with sodium fluoride. A solution is formed containing a water/alcohol soluble ethylene vinyl acetate copolymer, sodium fluoride, water and ethanol. The solution has the following composition by weight:

| ethylene vinylacetate copolymer | 20% |
|---|---|
| sodium fluoride | 0.0265% |
| water | 40% |
| ethanol | 39.9735% |

The yarn is coated by passing the floss through an apparatus similar to that of Example 1 except the heater is in an in-line alignment with the coating trough. The coating solution is applied at room temperature and the heater is at about 135° C. The level of coating and the floss is approximately 30 percent by weight with the sodium fluoride content being about 235 parts per million.

Example 3

As an alternative to the process of Example 1, the polymeric additive and the actives can be coated onto the yarn in the same step. A coating solution is formed containing a water/alcohol soluble ethylene vinyl acetate copolymer, sodium fluoride, water and ethanol. The solution has the following composition by weight:

| ethylene vinylacetate copolymer | 20% |
|---|---|
| sodium fluoride | 0.0265% |
| water | 40% |
| ethanol | 39.9735% |

The yarn is coated by passing the floss through an apparatus similar to that of Example 1 with trough 23 containing this coating solution. The coating solution is applied at room temperature and the heater chamber 30 is at about 135° C. The level of coating and the floss is approximately 26 to 30 percent by weight with the sodium fluoride content being about 225 to 250 parts per million.

What is claimed is:

1. A texturized dental floss comprising a texturized yarn having a thickness if about 10 to about 40 mm throughout its length at relaxation and a thickness of about 1 to about 4 mm at a tension of more than about 10 grams.

2. A texturized dental floss as in claim 1 wherein said texturized yarn has a coating of a water soluble polymer or a non-water soluble polymer.

3. A texturized dental floss as in claim 1 wherein said dental floss has a coating thereon of a substance selected from the group consisting of medicants, colorants and flavorants.

4. A texturized dental floss as in claim 3 wherein said medicant is selected from the group consisting of fluoride, desensitizing agents, anti-plaque agents, anti-tartar agents, anti-bacterials and coagulants.

5. A texturized dental floss as in claim 1 wherein said texturized yarn has an elongation of up to about 150 percent.

6. A texturized dental floss as in claim 1 wherein the cross-section of said yarn under tension is reduced to about as low as 10 percent of the cross-sectional diameter of the yarn in a non-tensioned condition.

7. A method for making a texturized dental floss comprising coating a texturized yarn with an agent to stabilize said yarn from shredding and fraying during use as a floss, said coating being applied to said yarn and cured thereon while said yarn over its full length is in an essentially relaxed and minimum tension condition whereby said floss has a thickness of about 10 mm to about 40 mm at relaxation and a thickness of about 1 mm to about 4 mm at a tension of more than about 10 grams.

8. A method as in claim 7 wherein said yarn is conveyed into and through a coating bath at a tension sufficient only to move said yarn through said coating bath and thereafter through a curing chamber at a tension sufficient only to move said yarn through said curing chamber.

9. A method as in claim 8 wherein said yarn moves essentially vertically, downwardly through said curing chamber.

10. A method as in claim 9 wherein said yarn moves downwardly to said curing chamber under gravitational forces.

11. A method as in claim 8 wherein said coating bath contains a substance selected from the group consisting of medicants, colorants and flavorants.

12. A method as in claim 11 wherein said medicant is selected from the group consisting of fluoride, desensitizing agents, anti-tartar agents, anti-bacterials and coagulants.

13. A method as in claim 8 wherein said yarn after coating is propelled along through contact with a paddle roller.

14. A method as in claim 8 wherein said coated texturized yarn is suspended free of contact with any surfaces in a substantially vertical orientation within a curing zone during the curing of said coating on said texturized yarn.

15. A method as in claim 7 wherein said agent to stabilize said yarn is a photopolymerizable polymer.

16. A method as in claim 15 wherein said photopolymerizable polymer is a polyurethane.

17. A method as in claim 7 wherein said agent to stabilize said yarn is a polymer dissolved in a solvent.

18. A method as in claim 17 wherein the dissolved polymer is a nylon.

19. A method as in claim 7 wherein said yarn having a cured coating thereon is wound onto a spool at a minimal tension.

20. A method as in claim 7 wherein said yarn with a cured coating is coated with a substance selected from the group consisting of medicants, colorants and flavorants.

21. A method as in claim 20 wherein said medicant is selected from the group consisting of fluoride, desensitizing agents, anti-tartar agents, anti-bacterials and coagulants.

22. A method as in claim 7 wherein said dental floss over its full length has an elongation of up to about 150 percent.

23. A method as in claim 7 wherein said texturized yarn during coating through the curing of said coating contacts rollers on only one surface.

* * * * *